(12) United States Patent
Jackson et al.

(10) Patent No.: US 6,248,796 B1
(45) Date of Patent: Jun. 19, 2001

(54) METHOD FOR PRODUCTION OF MIXED ALCOHOLS FROM SYNTHESIS GAS

(75) Inventors: Gene R. Jackson, Arvada, CO (US); Devinder Mahajan, South Setauket, NY (US)

(73) Assignee: PowerEnerCat. Inc., Lakewood, CO (US)

( * ) Notice: Subject to any disclaimer, the term of this patent is extended or adjusted under 35 U.S.C. 154(b) by 0 days.

(21) Appl. No.: 09/438,333

(22) Filed: Nov. 13, 1999

Related U.S. Application Data

(60) Provisional application No. 60/108,364, filed on Nov. 13, 1999.

(51) Int. Cl.$^7$ .................................................. C07C 27/00
(52) U.S. Cl. ........................................... 518/714; 518/700
(58) Field of Search ....................................... 518/700, 514

(56) References Cited

U.S. PATENT DOCUMENTS 4,752,623 * 6/1988 Stevens et al. ...................... 518/514

OTHER PUBLICATIONS

Mdleleni et al. J. Amer. Chem. Soc. 120, 6189–6190, Jun. 1998.*

* cited by examiner

*Primary Examiner*—Johann Richter
*Assistant Examiner*—J. Parsa
(74) *Attorney, Agent, or Firm*—Donald W. Margolis

(57) ABSTRACT

A method for production of mixed alcohols by using a sulfided transition metal catalyst selected from Group VI metals; nano-sizing the metal catalyst during its synthesis; suspending the catalyst in solvents to form a slurry; adding, a sulfur containing material to extend catalyst life; and contacting this slurry with carbon monoxide and hydrogen at 200–325° C. and 500–3000 psig pressure.

2 Claims, 1 Drawing Sheet

METHOD FOR PRODUCTION OF MIXED ALCOHOLS FROM SYNTHESIS GAS

RELATED U.S. APPLICATION DATA

This application claims the benefit of United States Provisional Application Ser. No. 60/108,364, filed Nov. 13, 1999, for A NOVEL METHOD FOR PRODUCTION OF MIXED ALCOHOLS FROM SYNTHESIS GAS.

BACKGROUND OF THE INVENTION

1. Field of the Invention

The present invention relates to a novel slurry-phase method to produce mixed alcohols from synthesis gas by utilizing a nanosized catalyst. The catalyst is activated by nanosizing and sulfiding during catalyst preparation.

2. Discussion of the Prior Art

Synthesis gas, hereinafter "syngas" is produced from any organic/carbonaceous source, such as, but not limited to municipal solid waste (MSW), refuse derived fuel (RDF), biogas from a digester, sewage sludge, chicken manure, turkey manure, other animal and agricultural waste, corn stover, switch grass, timber, grass clippings, construction demolition materials, cotton gin waste, biomass, landfill gas, natural gas and the like. The catalytic production of mixed alcohols from synthesis gas is a well established route and the literature contains numerous examples pertaining to this transformation. Of particular interest is a method described in U.S. Pat. Nos. 4,675,344; 4,749,724; 4,752,622; 4,752,623; and 4,762,858, all originally assigned to Dow Chemical Company. These patents describe, in general, a micron-size supported catalyst based on molybdenum disulfide ($MoS_2$). Mixed alcohols, primarily $C_1$–$C_4$, i.e. methanol—butanol, are produced in good yields when the Dow catalyst is used in a packed column or fluidized bed. The best yield of oxygenates fraction is approximately 20%, on a $CO_2$-free basis, with up to 85% selectivity to mixed alcohols. The rate of 0.1–0.4 grams product/gram catalyst/hour is claimed by the use of the Dow catalysts at 240–325° C. reaction temperature and 700–3000 psig. The above Dow patents and the references discussed and cited therein are incorporated by reference in this application.

Review of the above noted prior art and references will show that a process and catalyst that improves upon conditions of high temperature and high pressure conversion of synthesis gas to mixed alcohols, and which provides a higher conversion rate of synthesis gas to mixed alcohols per pass over/through the catalyst are highly desirable, especially for commercial applications.

For commercial application, a process that improves upon conditions of high temperature and high pressure and allows higher conversion per pass are highly desirable. To make a commercially significant alcohol process the catalyst must be highly efficient as well as the conditions in which the catalyst operates. The efficient catalyst must yield a high ratio of mass of product per given mass of catalyst in a given period of time. The catalyst must be stable and active over long periods of time before regeneration or replacement of the catalyst is required. When the feed gas has a low ratio, ideally when the $H_2$/CO ratio is less than 2 to 1, the catalyst will be highly selective to produce a commercial product to avoid purification or removal and disposal of by-products with the addition of a distillation tower that will split the product into two or more product streams.

When the mixture is used as a neat fuel for automobiles the presence of $C_1$ alcohol, i.e. methyl alcohol, is more beneficial than when the alcohols are used as a commercial blend in gasoline. As used in this application, the weight ratio of methanol or $C_1$ alcohol to $C_2$ + alcohols means the higher alcohols, such as ethanol, propanols, butanols, etc., taken as a whole for calculation purposes. This number may be calculated by determining the weight fraction of methanol in the mixed alcohols. The esters or ethers portion of the alcohol mix are not included in either the $C_1$ to $C_2$+ numbers. It is therefore understood that it would be beneficial to prepare mixed alcohols, primarily $C_1$–$C_4$, from synthesis gas derived from any carbonaceous source. It would also be beneficial to produce mixed alcohols in a highly efficiently manner by a catalytic method, i.e. in high yield per pass to avoid gas recycle under mild conditions of temperature and pressure.

SUMMARY OF THE INVENTION

It is therefore an object of the present invention to prepare mixed $C_1$–$C_4$, alcohols, primarily from synthesis gas derived from any carbonaceous source.

It is therefore an object of the present invention to produce mixed alcohols in a highly efficient manner by a catalytic method, having a high yield per pass to avoid gas recycle under mild conditions of temperature and pressure.

The present invention provides a novel method for producing mixed alcohols by combining one or more of the following steps. First a catalyst is selected from the Group VI metals, namely Cr, MO, W and mixtures thereof. Next, the selected metal is nanosized to a mean particle diameter (MPD) of less than about 100 nm. Nanosizing the metal is an especially important feature of the present invention, in that nonosizing provides more surface area per unit volume of the metal, thereby enhancing the reaction rates. The nanosized metal catalyst is then sulfided to enhance its resistance to the catalyst poisons that are normally present in syngas.

Nanosizing of the metal catalyst can be achieved by a variety of methods. One preferred method of nanosizing is sonication of a carbonyl precursor of the metal. An example of nanosizing is found in the literature reference (Mdleleni er al. J. Amer. Chem. Soc. 120 6189–6190 (1998)). Catalyst-sulfiding can be achieved during or after the nanosizing procedure.

During the alcohol production from syngas production, the nanosized, sulfided Group VI metal catalyst may be unsupported, or it may be supported on a high surface area support such as carbon, alumina, silica or the like. In either arrangement the nanosized catalyst is suspended in an inert solvent, such as a high molecular weight hydrocarbon solvent such as ethylflo-164, to form a slurry. Suspension of the nanosized catalyst allows excellent heat management during the thermal operations, and this in turn increases mixed alcohol product yield.

The syngas is then passed through the catalyst slurry to produce alcohols in the product stream. The input syngas composition varies from $H_2$/CO of 1/4 to 3/1 though other gaseous impurities may be present. In order to enhance reaction rates, additives that make the Group VI metal catalyst more susceptible to initial carbon monoxide attack are preferred. The operating temperature range is from about 200° C. to less than about 300° C. The operating pressure ranges is from about 500 to about 3000 psig. The space-time-yield (STY) of product mixed alcohols is better than those claimed by any known commercial methods, that is greater than about 0.4 gram product/gram catalyst/hr. In order to enhance catalyst life, a small amount of sulfur source is added either directly to the reaction vessel in which alcohols are being continuously produced, or to the incoming syngas stream.

By combining these steps, using a novel catalyst in a novel process efficiently produces mixed alcohols. In one embodiment of this invention, nanosized particles (MPD<100 nm) of molybdenum are produced by the sonication method and are suspended in a hydrocarbon solvent having a carbon chain length of 30. A sulfur source, being elemental sulfur itself, is added to the slurry. By contacting the slurry with a stream of carbon monoxide and hydrogen in ½ ratio at temperature in the range of about 250 to about 280° C. and pressure in the range of about 500 to about 200 psig pressure, mixed alcohols are produced in the product stream with STY surpassing 0.4 grams product/gram catalyst/hour reported with the known prior art technology.

These and other objects of the present invention will become apparent to those skilled in the art from the following detailed description and accompanying drawings, showing the contemplated novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawing which is incorporated in and form a part of this specification illustrate complete preferred embodiments of the present invention according to the best modes presently devised for the practical application of the principles thereof, and in which.

DETAILED DESCRIPTION OF THE PROCESS

Figure 1:
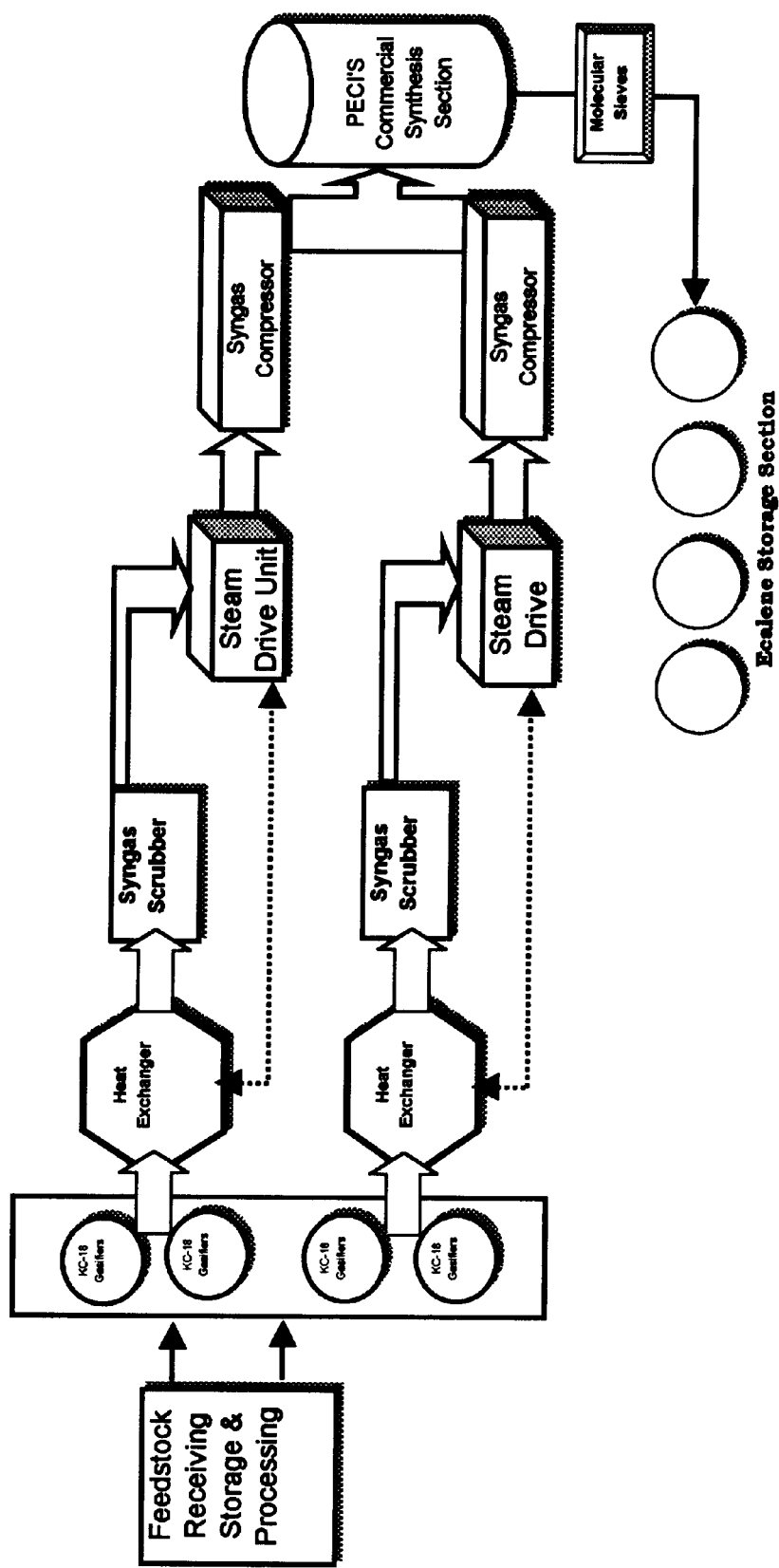
FIG. 1 is a conceptual diagram of the entire process from syngas feed to mixed alcohol storage.

During the municipal solid waste treatment process the waste material is sorted to be free of all metals including aluminum, and glass. Plastics may or may not be separated depending upon the value of the recycled plastics at the time. The material is then gasified, cooled and cleaned. The synthesis gas that is produced by this process will be at a ratio that will vary from $H_2/CO$ of 1:1.2 to 1:2 although other gaseous impurities may be present. The gaseous material will then be compressed at approximately 100° F. at a pressure from about 500 to about 1000 psig and passed through the novel nanosized suspended Group VI metal to produce mixed alcohols with STY surpassing 0.4 grams product/gram catalyst/hour.

The digestion of manure from all types of animals produces syngas, although manure from diaries and hog farms and feedlots have been targeted. The digestion process will yield several more moles of methane than of carbon dioxide. A commercially available partial oxidation unit then disassociates the methane gas. The syngas from the partial oxidation unit is expected to yield a 1:1 ratio of $H_2$ to CO. The gaseous material will then be compressed at approximately 100° F. at a pressure from about 500 to about 1000 psig and passed through the novel nanosized suspended Group VI metal to produce mixed alcohols with STY surpassing 0.4 grams product/gram catalyst/hour.

Where waste rubber, such as tires and or autofluff become plentiful and needs to be processed, a pyrolyzer will be utilized to produce syngas. The syngas ratio can vary widely with these processes and the material being processed will also vary. The syngas from the pyrolyzer unit is expected to yield a 1:1 or 1.1.4 ratio of $H_2$ to CO.

A steam reformer, such as those found on a typical methanol plant, may be utilized with a recirculation of the hydrogen back into the process to be utilized for makeup heat as well as additional carbon monoxide being manufactured from the carbon dioxide through the hydrogen burner unit furnished by others in the process.

To provide a commercially significant alcohol process, the present invention uses a catalyst and conditions which are highly efficient. To be efficient the catalyst must yield a high ratio of mass product per given mass of catalyst in a given period of time. The catalyst must be stable and highly active for long periods of time between regenerations. This is particularly difficult to accomplish when the $H_2/CO$ ratio of feed gas is low, such as less than about 2 to 1. Ideally the catalyst is highly selective to commercial product to avoid purification or removal and disposal of by-products and to avoid separation into two or more product streams. The use of a partial oxidation unit before placing the syngas stream into the catalyst slurry bed, or other catalyst presentation method, is chosen to make the mixed alcohol and greatly enhances the ability of the catalyst to select the desired ratio of alcohols.

The replacement or the use of the alcohol as an additive to gasoline the ratio of the $C_1$ to $C_2$+ alcohols should be no greater than a certain amount. As used in this application, the ratio of $C_1$ to $C_2$+ means the weight ratio of methanol to higher alcohols such as ethanol, propanols, butanols, and the like, taken as a whole. This number may be easily calculated by determining the weight fraction of methanol in the mixed alcohols with the desired mixture for mixing with gasoline to be almost zero on the $C_1$ alcohols.

Through all of these processes it is desired that ethyl alcohol be a major product constituent, with the yield of methanol at a very small portion of the overall product. While this process is an advance over the art it would be advantageous if it were possible to increase the $C_2$ and other alcohols and decrease the percentage of methanol in the mixes made when using the mix as a blend in gasoline. Under preferred conditions, alcohols may be obtained in about 95 percent per pass of the $H_2/CO$ syngas at any preferred ratio. The selectivity of the $C_2$ and other higher alcohols are preferred and should be obtained with this invention.

The space velocity of the hourly rate that the $H_2/CO$ gas passes a given volume of catalyst in an hour's time (GHSV) is a measure of the volume of the hydrogen plus carbon monoxide gas at a standard temperature and pressure. The selectivity of the alcohols generally increase as the space velocity increases, however conversion of the carbon monoxide decreases as the space velocity increases. Some of these gases may be recycled in the reaction; however, the recycle ratio of zero is within the scope of the invention because of the highly active catalyst.

Where shut-in natural gas, pipeline natural gas or landfill gas is plentiful it needs to be processed by other means than cleaning it to enter the market place via the pipeline. The syngas ratio will be fairly stable in all of these applications but should yield a very stable syngas. An autotherm reformer or partial oxidation unit will be utilized to produce syngas that is expected to yield a 1:1 or 1:1.2 ratio of $H_2$ to CO.

FIG. 1 is a conceptual diagram of the entire process from syngas feed to mixed alcohol storage. The mixed alcohol is referred to be its trademark "ECALENE".

It will therefore be appreciated that in the practice of the processes and in the use of the catalysts of the present invention, a novel process results that efficiently produces mixed alcohols from syngas.

What is claimed is:

1. Methods for the production of mixed alcohols which comprises the steps of:

using a sulfided, nanosized transition metal catalyst selected from Group VI metals;

nanosizing the Group VI transition metal catalyst;

suspending the catalyst in a solvent to form a slurry;

contacting said slurry with gases comprising carbon monoxide and hydrogen at a temperature in the range of about 250 to about 325° C. and at a pressure in the range of about 500 to about 3000 psig, to thereby produce mixed alcohols.

2. The method of claim 1 wherein the nanosized Group VI transition metal catalyst is sulfided prior to its use in producing mixed alcohols from gases comprising carbon monoxide and hydrogen.

* * * * *